US008184898B2

(12) United States Patent  
Hallock et al.

(10) Patent No.: US 8,184,898 B2  
(45) Date of Patent: May 22, 2012

(54) ANALYSIS OF LEADED COMPONENTS

(75) Inventors: Donald A. Hallock, Poughkeepsie, NY (US); Vincent P. Mulligan, Wappingers Falls, NY (US); Joseph P. Paul, Hopewell Junction, NY (US); James I. Paradies, Clintondale, NY (US); Nandu N. Ranadive, Wappingers Falls, NY (US)

(73) Assignee: International Business Machines Corporation, Armonk, NY (US)

( * ) Notice: Subject to any disclaimer, the term of this patent is extended or adjusted under 35 U.S.C. 154(b) by 651 days.

(21) Appl. No.: 12/415,036

(22) Filed: Mar. 31, 2009

(65) Prior Publication Data

US 2010/0246935 A1 Sep. 30, 2010

(51) Int. Cl.  
*G06K 9/00* (2006.01)

(52) U.S. Cl. .................. 382/146; 382/149; 382/150

(58) Field of Classification Search .......... 382/145, 382/146, 147, 149, 150  
See application file for complete search history.

(56) References Cited

U.S. PATENT DOCUMENTS

| | | | |
|---|---|---|---|
| 4,926,452 A | 5/1990 | Baker et al. | |
| 6,185,273 B1 | 2/2001 | Sperschneider | |
| 6,853,744 B2 | 2/2005 | Mueller et al. | |
| 7,231,013 B2 | 6/2007 | Meyer | |
| 7,239,740 B1 | 7/2007 | Fujieda | |
| 7,366,321 B2 | 4/2008 | Usikov | |
| 7,738,093 B2 * | 6/2010 | Alles et al. | 356/237.5 |
| 7,801,353 B2 * | 9/2010 | Almogy et al. | 382/141 |
| 2009/0232386 A1 * | 9/2009 | Sano | 382/146 |

OTHER PUBLICATIONS

C. Neubauer et al.; "Improving X-Ray Inspection of Printed Circuit Boards by Integration of Neural Network Classifiers;" IEEE/CHMT International Manufacturing Technology Symposium, 1993, pp. 14-18.  
Hideaki Doi et al.; "Real-Time X-ray Inspection of 3-D Defects in Circuit Board Patterns;" IEEE, 1995, pp. 575-582.  
Y.J. Roh et al.; "Inspection of Ball Grid Array (BGA) Solder Joints Using X-Ray Cross-Sectional Images;" Part of the SPIE Conference on Machine Vision Systems for Inspection and Metrology VIII, SPIE vol. 3836; Sep. 1999; pp. 168-178.  
F. Voci et al.; "Fuzzy Inference Filter and Morphological Operators for Short Circuits Detection in Printed Circuit Board;" IEEE, 2002, pp. 672-677.  
A. Teramoto et al.; "Development of an Automated X-Ray Inspection Method for Microsolder Bumps;" 2005 International Symposium on Electronics Materials and Packaging (EMAP2005); Dec. 11-14, 2005; IEEE, pp. 21-26.

\* cited by examiner

*Primary Examiner* — John Strege  
(74) *Attorney, Agent, or Firm* — Cantor Colburn LLP; Steven Bennett

(57) ABSTRACT

A system to facilitate analysis of component leads is provided and includes a device to form a picture of the leads, from which an image is extracted, to apportion the image and to perform first and second scans of the portions, and a processor, including a memory unit having a set of computer-readable executable instructions stored thereon, which, when executed, cause the processor to receive data of each scan, to establish a rule, based on the data of the first scan of any one portion, governing when to judge that the data of the second scan of the one portion indicates a defect, to determine rule compliance for each of the second scans, to judge that any one second scan in a non-compliance state indicates a defect, and to report a location of the defect. A display unit displays the report to a user.

18 Claims, 4 Drawing Sheets

ANALYSIS OF LEADED COMPONENTS

BACKGROUND

Aspects of the present invention are directed to leaded components and, more particularly, to a system and method to facilitate analysis of leaded components.

The detection of defects in leaded components has long employed x-rays for the production of images of the leads of the components that can be inspected either manually or by a computing device. A problem exists, however, in that shorts and low solder conditions have not been able to be accurately and reliably detected.

For example, where the x-ray images of the leads are manually inspected, human error frequently led to defects being unexamined or missed completely. As a result, the quality and reliability of leaded components has been limited. On the other hand, using a computing device to detect the defects frequently resulted in false positive or false negative determinations. In false positive determinations, the computing device judged defective leads to be non-defective because the computing device was unable to recognize defects efficiently. On the other hand, false negative determinations were made because the computing device was unable to differentiate between actual defects and image imperfections and/or noise.

SUMMARY

In accordance with an aspect of the invention, a system to facilitate analysis of component leads is provided and includes a device to form a picture of the leads, from which an image is extracted, to apportion the image and to perform first and second scans of the portions, and a processor, including a memory unit having a set of computer-readable executable instructions stored thereon, which, when executed, cause the processor to receive data of each scan, to establish a rule, based on the data of the first scan of any one portion, governing when to judge that the data of the second scan of the one portion indicates a defect, to determine rule compliance for each of the second scans, to judge that any one second scan in a non-compliance state indicates a defect, and to report a location of the defect. A display unit displays the report to a user.

In accordance with another aspect of the invention, a method to facilitate analysis of component leads is provided and includes forming a picture of the leads, from which an image is extracted, apportioning the image and performing first and second scans of the portions of the image at a device, receiving, at a processor, data of each scan, and, at the processor, establishing a rule, based on the data of the first scan of any one portion, governing when to judge that the data of the second scan of the one portion indicates a defect, determining rule compliance for each of the second scans, judging that any one second scan in a non-compliance state indicates a defect, and reporting a location of the defect and displaying the report a user at a display unit disposed in signal communication with the processor.

In accordance with yet another aspect of the invention, a method to facilitate analysis of component leads is provided and includes forming a picture of the leads, from which an image is extracted, apportioning the image, performing first and second scans of the portions of the image, establishing a rule, based on the data of the first scan of any one portion, governing when to judge that the data of the second scan of the one portion indicates a defect, determining rule compliance for each of the second scans, judging that any one second scan in a non-compliance state indicates a defect, reporting a location of the defect and displaying the report to a user.

BRIEF DESCRIPTIONS OF THE SEVERAL VIEWS OF THE DRAWINGS

The subject matter regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

DETAILED DESCRIPTION

Figure 1:
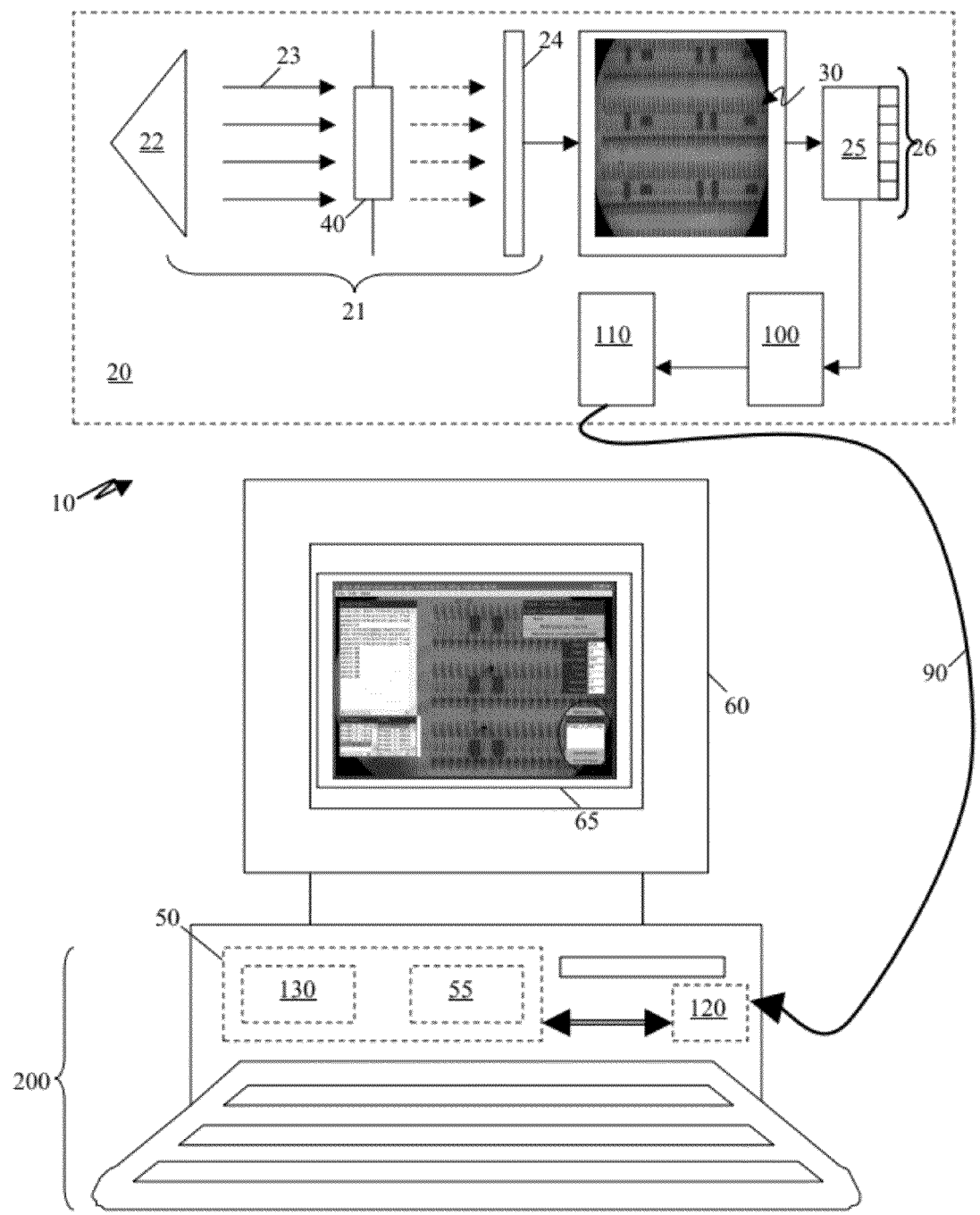
FIG. 1 is a schematic view of a system to facilitate analysis of component leads in accordance with embodiments of the present invention.
Figure 2:
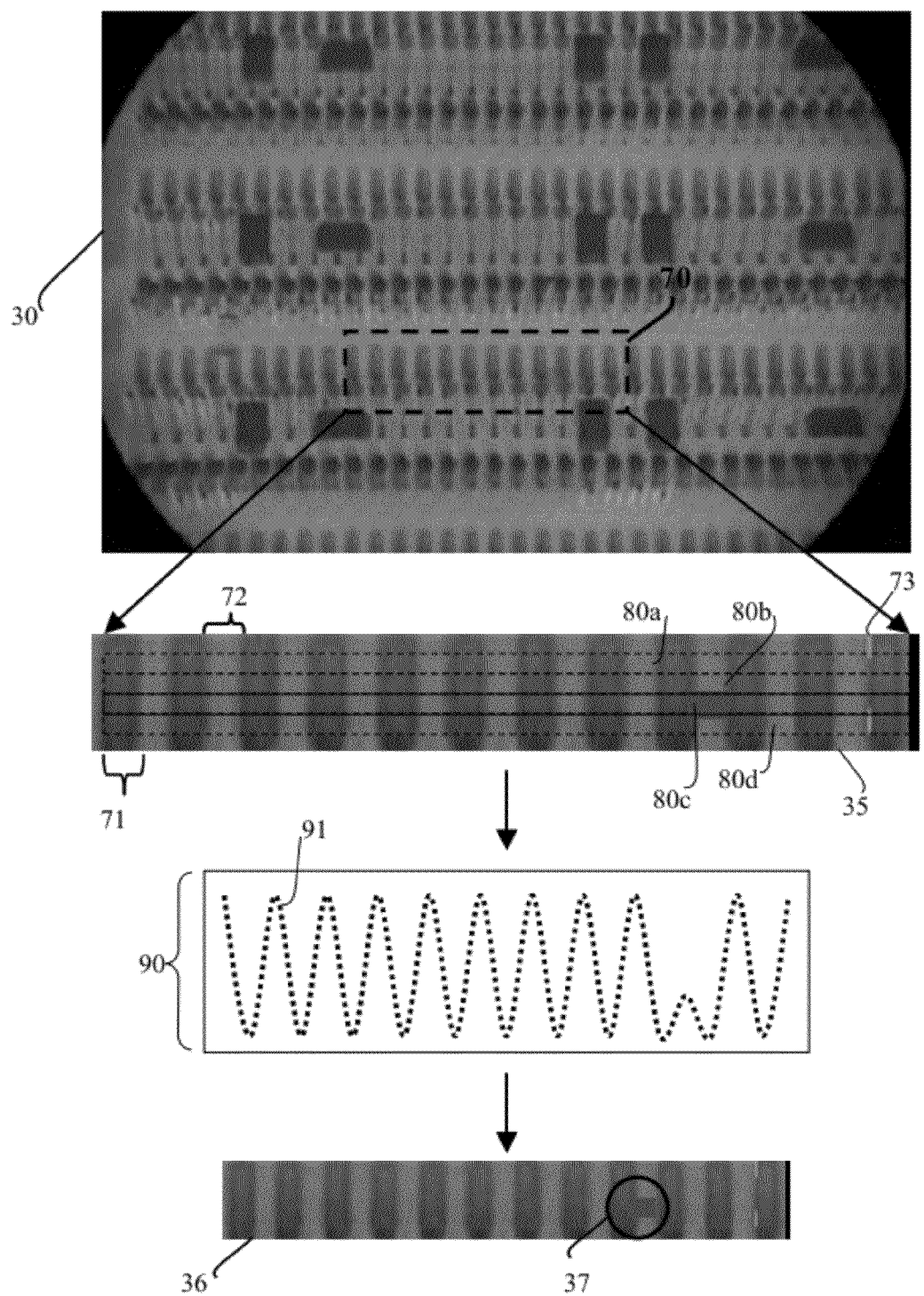
FIG. 2 is a flow diagram illustrating a graphical analysis of an image of component leads in accordance with embodiments of the present invention.

With reference to FIGS. 1 and 2, a system 10 to facilitate analysis of component leads 40 is provided. The system 10 includes a device 20, a processor 50 and a display unit 60. The device 20 is configured to form a picture 30 of the leads 40 of, e.g., a printed circuit board (PCB) or some other similar component or object, in which a defect that needs to be identified and corrected may be an excessive or, alternately, a deficient amount of solder material at a particular lead 40. The device 20 is further configured to form an image 35, which is extracted from the picture 30, to apportion the image 35 into portions 80a, 80b 80c and 80d thereof, and to perform at least first and second scans of each of the portions 80a, 80b 80c and 80d such that data reflective of the scanned images can be generated and output to the processor 50.

The processor 50 includes memory unit 55, including memory units such as random access memory (RAM) units and read-only memory (ROM) units, on which a set of executable instructions are stored. The executable instructions, when executed, cause the processor 50 to be receptive of data that is reflective of each scan. The executable instructions further cause the processor 50 to establish a rule, based on the data of the first scan of any one portion 80a, 80b 80c or 80d, that governs when to judge that the data of the second scan of the one portion 80a, 80b 80c or 80d is indicative of a defect in any one of the leads 40, to determine rule compliance for each of the second scans, and to judge that any one second scan, which is found to be in a non-compliance state, is indicative of a defect.

The executable instructions further cause the processor 50 to generate a report of a location of the defect. In an embodiment, this may involve the processor 50 marking the image 35 at a location of the defect with a mark 37. The image 35, having been marked in this manner, is then rendered by, e.g., a graphic driver or some other suitable display driver, as a marked image 36. The display unit 60, which is disposed in signal communication with the processor 50, is configured to be driven by the processor 50 to display the report to a user of the system 10. Where the processor 50 marks the image 35, the processor 50 drives the display unit 60 to display the marked image 36 to the user of the system 10.

The device 20 may include an x-ray machine 21 or some other image forming apparatus. Where the device 20 is an x-ray machine, the device 20 includes an emitter 22 that emits x-ray radiation 23 toward the leads 40 with some radiation being allowed to propagate toward film 24 and with other radiation impacting leads 40 and/or solder material and being reflected away from the film 24. In this way, a two-dimensional representation of the leads 40 is formed on the film 24 as the picture 30. As such, if any of the leads 40 are defective as a result of, e.g., having excessive or deficient amounts of solder, such defects will be represented in the picture 30 as being relatively dark or light areas of the picture 30 that would normally not be as dark or as bright.

The device 20 may further include a scanning device 25, such as a scanner. The scanning device receives the picture 30 on the film 24 and forms the image 35 from the picture 30. As shown in FIG. 1, the device 20 may include the x-ray machine 21 and the scanning device 25 as a single unit. However, it is understood that embodiments exist in which the x-ray machine 21 and the scanning device 25 may also be physically separate from one another and disposed in signal communication with one another.

With reference to FIG. 2, the picture 30 is formed into the image 35 by the scanning device 25 focusing in on only the section 70 (see the dotted line box of FIG. 2) of the picture 30 that is currently being analyzed at any one time. Alternately, the image 35 may be formed by the scanning device 25 effectively cutting away those portions of the picture 30 that are not currently being analyzed. In any case, the image 35 is a representation of only a subset of the leads 40 that are currently being analyzed and does not include leads 40 that are not being analyzed or any other components that are shown in the picture 30. Thus, the image 35 is actually made up of an array of relatively dark bands 71 and light bands 72 that are representative of lead 40 areas with solder and without solder, respectively.

In an embodiment of the invention, the size of the image 35 will be sufficient to include a group of 11 dark and light bands 71 and 72 from left to right, as shown in FIG. 2 up to the line marker 73. However, it is understood that this number of dark and light bands 71 and 72 is merely exemplary and that other numbers of bands may be included within the image 35.

Once the image 35 is formed from the picture 30, the scanning device 25 of the device 20 performs at least first and second scans of the portions 80a, 80b, 80c and 80d of the image 35 from left to right with each of the portions 80a, 80b, 80c and 80d being set at a preselected thickness. In an embodiment of the invention, this preselected thickness is 4 pixels thick such that the device 20 is required to scan the image 35 at multiple positions along the height of the image 35 in order to complete an entire scan of the image 35. In this way, since the number of total portions of the image 35 is (the pixel thickness of the image)/4, the scanning of each portion of the image 35 is completed in a relatively short time. Moreover, since the portions 80a, 80b, 80c and 80d are only 4 pixels thick, small defects within the leads 40 are identifiable. Still further, with the portions 80a, 80b, 80c and 80d being 4 pixels thick (as opposed to 1-3 pixels thick), imperfections in the picture 30 or the image 35 that do not amount to defects are ignored along with noise.

It is, nevertheless, understood that the 4 pixel thickness of the portions 80a, 80b, 80c and 80d is merely exemplary and that other thicknesses may be used. For example, it is possible that thicknesses of less than 4 pixels may be used as long as the problems of scanning imperfections and/or noise are overcome. Moreover, rather than having a preselected thickness programmed, the thickness may be set for each portion 80a, 80b, 80c and 80d as being based on an overall thickness of the image 35 and time requirements or as being based on scan speed and accuracy requirements and/or other current conditions.

Once a first or a second scan of any of the portions 80a, 80b, 80c or 80d of the image 35 is completed, the device 20 generates data 90 that is reflective of the scanned portion of the image and outputs that data 90 to the processor 50, which may be a component of a computing device 200, such as a personal computer (PC) or a workstation in an industrial application. To this end, the device 20 may further include an analog to digital (A/D) converter 100 and an input/output (I/O) unit 110. The A/D converter 100 converts analog data of the picture 30 into digital data. The I/O unit 110, which is coupled to the A/D converter 100, then transmits the digital data as the data 90 to the processor 50. The data 90 is subsequently received at the processor 50 via an I/O unit 120 disposed at the computing device 200.

Where the data 90 is reflective of a first scan of any one portion, e.g., portion 80a of the image 35, the data 90 may include actual gray scale values of the dark bands 71 and the light bands 72 and/or a moving average 91 of the gray scale values across the left to right length of the portion 80a, as shown in FIG. 2. The processor 50 then analyzes the data and establishes a rule governing when to judge that the scan is indicative of a defect in the leads 40 represented in the portion 80a. This rule is specifically defined, in this case, for the first scan of the portion 80a and cannot and will not be used for any other scan other than the second scan of the portion 80a, which is generally to be conducted substantially immediately after the completion of the first scan. In fact, once the rule is employed in the analysis of the corresponding second scan, the rule may be discarded from the memory 55. In this way, since the processor 50 may re-establish rules for portion 80a after each first scan thereof, the processor 50 accounts for the fact that the device 20 does not necessarily form the picture 30 or the image 35 in the same manner in every instance. Thus, the processor 50 accounts for the fact that the data 90, such as the moving average 91 of the gray scale values may be different for each first scan of the portion 80a of the image 35.

In one embodiment of the invention, the rule established by the processor 50 may be that the moving average 91 of the gray scale values of the portion 80a of the image 35 is abnormal at some point along the left-to-right length of the image 35. Here, the processor 50 recognizes that the moving average is a sin wave that has an average amplitude. From this, the processor 50 determines a range of normal amplitudes for each period of the wave and judges whether any period of a wave for the portion 80a fails to reach that normal amplitude. Such a failure would represent an abnormal section of the portion 80a of the image 35 and the processor 50 would then judge that the leads 40 associated with the abnormal section may be defective.

In another embodiment of the invention, the rule may be that the moving average 91 will have a certain number of data points for each left-to-right length of the image 35 and that a normal section of the image 35 will have a given number of data points increasing or decreasing after a change of direction whereas an abnormal section will have a redirection of the moving average 91 shortly after a previous redirection. This is shown in the schematic graph of the moving average 91 in FIG. 2. Again, such a redirection of the wave would represent an abnormal section of the portion 80a of the image 35 and the processor 50 would then judge that the leads 40 associated with the abnormal section may be defective.

Where the data 90 is reflective of a second scan of the portion 80a, the data 90 may be similar to the data 90 of the first scan, however, in this case, the processor 50 determines whether the second scan complies with the rule established as being based on the data 90 of the first scan. That is, if the rule is that the moving average 91 will have a certain number of data points for each left-to-right length of the image 35 and the second scan indicates that this is not the case for the entire portion 80a, the processor 50 determines that the second scan does not comply with the rule. Accordingly, the processor 50 judges that the second scan of the portion 80a is indicative of a defect in the leads 40.

In accordance with an embodiment of the invention, the first and second scans of portion 80a are completed in series with the corresponding analyses being completed at the processor 50 before further scans of other portions of the image 35 are undertaken. Thus, the scanning of the various portions 80a, 80b, 80c and 80d may be performed in series. Alternately, the first scans for each of the portions 80a 80b, 80c and 80d may all be performed in parallel with one another with the second scans for each subsequently performed in parallel. In this case, the processor 50 completes the analysis of the entire image 35 at one time. In accordance with an embodiment of the invention, where the portions 80a, 80b, 80c and 80d are to be scanned in parallel, the scanning device 25 may be configured to simultaneously scan multiple portions of the image 35. That is, the scanning device 25 may include multiple scanners 26 arrayed along a thickness direction of the scanning device 25.

The processor 50 may further include a graphic driver 130 that allows the processor 50 to communicate with the display unit 60 and which drives the display unit 60 to display a graphical user interface (GUI) 65 to a user of the computing device 200. In accordance with embodiments of the invention, the GUI 65 may be a java frame or some other suitable computing environment and may be configured to allow the user to adjust and to rescan the image 35 and to document results as necessary. The GUI 65 includes the marked image 36 with the mark 37 being, e.g., a circle around the image of the defect, data tables and menu buttons. The menu buttons allow the user to conduct various operations including adjusting the image 35, rescanning the image 35 and documenting results for later reference or for use in improving the performance of the device 20.

Figure 3:
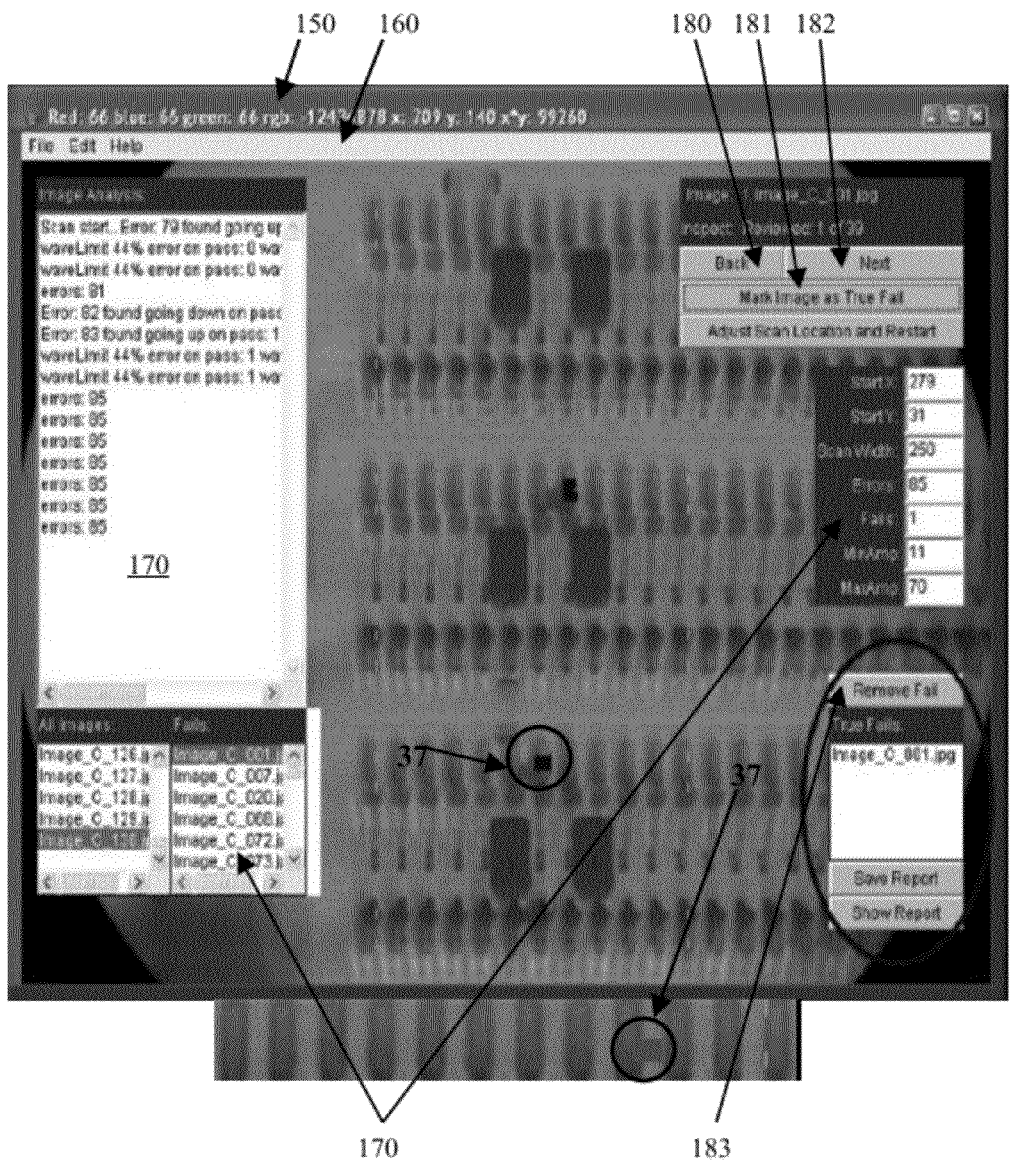
FIG. 3 is a view of a screenshot of a graphical user interface (GUI) in accordance with embodiments of the invention.

With particular reference to FIG. 3, an exemplary GUI 65 in accordance with embodiments of the invention includes a title bar 150 that describes the content displayed within the GUI 65, a menu bar 160 that allows the user to save and edit the contents of the GUI 65, data tables 170 that provide status information to the user and menu buttons 180-183 that allow the user to interact with the GUI 65. Among these, menu button 181 allows the user to mark an image of a defect as a true fail. When menu button 181 is actuated, the system 10 records that an image of a defect is regarded as a true fail. After a time during which several true fails and, in certain cases, false fails are recorded, the system 10 refines and/or updates the rule establishing operations executed by the processor 50. In so doing, the system 10 becomes increasingly accurate over time.

In accordance with another aspect of the invention, a method to facilitate analysis of component leads 40 is provided and includes forming a picture 30 of the leads 40, from which an image 35 is extracted, apportioning the image and performing first and second scans of the portions 80a, 80b, 80c and 80d of the image 35 at a device 20. The method further includes receiving, at a processor 50, data of each scan, and, at the processor 50, establishing a rule, based on the data of the first scan of any one portion, governing when to judge that the data of the second scan of the one portion indicates a defect, determining rule compliance for each of the second scans, judging that any one second scan in a non-compliance state indicates a defect, and reporting a location of the defect, such as by marking the image at a location of the defect. The method also includes displaying the report and/or the marked image to a user at a display unit 60 that is disposed in signal communication with the processor 50. In accordance with this aspect, the method may further include performing the first and second scans of each of the portions in series or, alternately, performing the first scans of each of the portions in parallel, and performing the second scans of each of the portions in parallel.

Figure 4:
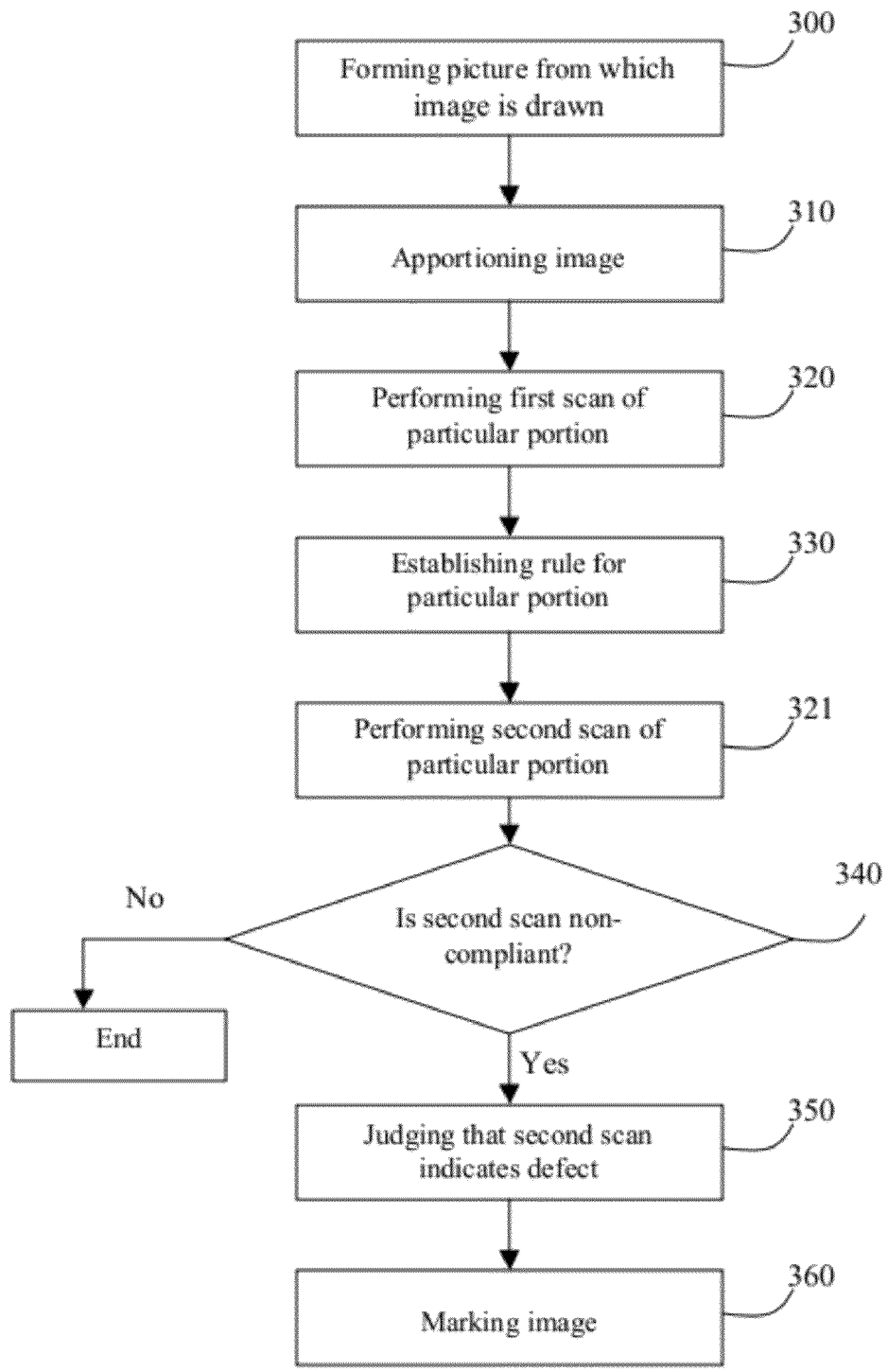
FIG. 4 is a flow diagram illustrating a method of facilitating analysis of component leads in accordance with embodiments of the present invention.

With reference to FIG. 4, in accordance with yet another aspect of the invention, a method to facilitate analysis of component leads 40 is provided and includes forming a picture of the leads, from which an image 35 is extracted 300, apportioning the image 310, performing first and second scans of the portions of the image 320, 321, establishing a rule, based on the data of the first scan of any one portion, governing when to judge that the data of the second scan of the one portion indicates a defect 330, determining rule compliance for each of the second scans 340, judging that any one second scan in a non-compliance state indicates a defect 350, reporting a location of the defect, such as by marking the image at a location of the defect, and displaying the report and/or the marked image to a user 360. Here again, the method may further include performing the first and second scans of each of the portions in series or, alternately, performing the first scans of each of the portions in parallel, and performing the second scans of each of the portions in parallel.

The methods disclosed above may be embodied as a computer and/or machine readable medium having a set of executable instructions stored thereon, which, when executed cause the computer and/or the machine to execute the methods.

In accordance with the aspects of the invention discussed above, a cycle time of the inspection process on P and Z Cassini boards has been reduced from around 35 to around 10 minutes. Of those 10 minutes, as an example, 8 minutes are spent generating 210 separate images of the Z Cassini boards. At the same time, an analysis of the results of the inspection process has shown that the system and method described above are highly accurate and, indeed, never fail to identify defects in leaded components.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular exemplary embodiment disclosed as the best mode contemplated for carrying out this disclosure, but that the disclosure will include all embodiments falling within the scope of the appended claims.

What is claimed is:

1. A system to facilitate analysis of component leads, the system comprising:
   a device to form a picture of the leads, from which an image is extracted, to apportion the image and to perform first and second scans of the portions of the image;
   a processor, including a memory unit having a set of computer-readable executable instructions stored thereon, which, when executed, cause the processor to receive data of each scan, to establish a rule, based on the data of the first scan of any one portion, governing when to judge that the data of the second scan of the one portion indicates a defect, to determine rule compliance for each of the second scans, to judge that any one second scan in a non-compliance state indicates a defect, and to report a location of the defect; and a display unit, in signal communication with the processor, to display the report to a user.

2. The system according to claim 1, wherein the device comprises an x-ray machine.

3. The system according to claim 1, wherein the device comprises a single machine.

4. The system according to claim 1, wherein the portions of the image are scanned in series.

5. The system according to claim 1, wherein the portions of the image are scanned in parallel.

6. The system according to claim 1, wherein the device scans the portions of the image from left to right.

7. The system according to claim 6, wherein the portions of the image are 4 pixels thick.

8. The system according to claim 1, wherein the display unit displays a graphical user interface (GUI) to the user.

9. The system according to claim 8, wherein the GUI is configured to allow the user to adjust and rescan the image and to document results.

10. The system according to claim 8, wherein the GUI comprises a java frame.

11. A method to facilitate analysis of component leads, the method comprising:
    forming a picture of the leads, from which an image is extracted, apportioning the image and performing first and second scans of the portions of the image at a device;
    receiving, at a processor, data of each scan, and, at the processor, establishing a rule, based on the data of the first scan of any one portion, governing when to judge that the data of the second scan of the one portion indicates a defect, determining rule compliance for each of the second scans, judging that any one second scan in a non-compliance state indicates a defect, and reporting a location of the defect; and
    displaying the report to a user at a display unit disposed in signal communication with the processor.

12. The method according to claim 11, further comprising performing the first and second scans of each of the portions in series.

13. The method according to claim 11, further comprising:
    performing the first scans of each of the portions in parallel; and
    performing the second scans of each of the portions in parallel.

14. The method according to claim 11, further comprising:
    receiving an input, at the processor, that the judging operation accurately identified the defect; and
    updating conditions for the operation of establishing the rule in accordance with the received input.

15. A method to facilitate analysis of component leads, the method comprising:
    forming a picture of the leads, from which an image is extracted;
    apportioning the image;
    performing first and second scans of the portions of the image;
    establishing a rule, based on the data of the first scan of any one portion, governing when to judge that the data of the second scan of the one portion indicates a defect;
    determining rule compliance for each of the second scans;
    judging that any one second scan in a non-compliance state indicates a defect;
    reporting a location of the defect; and
    displaying the report to a user.

16. The method according to claim 15, further comprising performing the first and second scans of each of the portions in series.

17. The method according to claim 15, further comprising:
    performing the first scans of each of the portions in parallel; and
    performing the second scans of each of the portions in parallel.

18. The method according to claim 15, further comprising:
    receiving an input that the judging operation accurately identified the defect; and
    updating conditions for the operation of establishing the rule in accordance with the received input.

* * * * *